(12) United States Patent
Eshoo et al.

(10) Patent No.: US 9,217,132 B2
(45) Date of Patent: Dec. 22, 2015

(54) MICROFLUIDIC TRANSDUCER

(75) Inventors: Mark W. Eshoo, Solana Beach, CA
(US); Jose R. Gutierrez, San Marcos,
CA (US); Jared J. Drader, Carlsbad,
CA (US); John Picuri, Carlsbad, CA
(US); Karl M. Cabrera, Cypress, CA
(US); Stanley Motley, Carlsbad, CA
(US); Thomas N. Chiesl, Hurcules, CA
(US)

(73) Assignee: IBIS BIOSCIENCES, INC., Carlsbad,
CA (US)

( * ) Notice: Subject to any disclaimer, the term of this
patent is extended or adjusted under 35
U.S.C. 154(b) by 936 days.

(21) Appl. No.: 13/355,261

(22) Filed: Jan. 20, 2012

(65) Prior Publication Data
US 2012/0190126 A1 Jul. 26, 2012

Related U.S. Application Data

(60) Provisional application No. 61/434,704, filed on Jan. 20, 2011.

(51) Int. Cl.
*G01N 1/28* (2006.01)
*B01L 3/00* (2006.01)
*C12M 1/00* (2006.01)
*C12N 1/06* (2006.01)
*C12N 13/00* (2006.01)

(52) U.S. Cl.
CPC .............. *C12M 47/06* (2013.01); *C12N 1/066*
(2013.01); *C12N 13/00* (2013.01); *Y10T 436/25*
(2015.01)

(58) Field of Classification Search
CPC ....... C12M 47/06; C12N 1/066; C12N 13/00;
Y10T 436/25
See application file for complete search history.

(56) References Cited

U.S. PATENT DOCUMENTS

| 5,750,341 A | 5/1998 | Macevicz |
| 5,969,119 A | 10/1999 | Macevicz |
| 6,013,445 A | 1/2000 | Albrecht et al. |
| 6,274,320 B1 | 8/2001 | Rothberg et al. |
| 6,306,597 B1 | 10/2001 | Macevicz |
| 6,664,079 B2 | 12/2003 | Ju et al. |
| 6,833,246 B2 | 12/2004 | Balasubramanian |
| 6,878,540 B2 | 4/2005 | Pourahmadi et al. |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,264,929 B2 | 9/2007 | Rothberg et al. |

(Continued)

OTHER PUBLICATIONS

Belgrader, Phillip et al. "A minisonicator to rapidly disrupt bacterial spores for DNA analysis." Analytical Chemistry (1999) 71 4232-4236.*

(Continued)

*Primary Examiner* — Christopher A Hixson
(74) *Attorney, Agent, or Firm* — David A. Casimir; Casimir Jones, S.C.

(57) ABSTRACT

Provided herein are apparatuses and methods for fragmenting nucleic acids or disrupting cells. For example, some embodiments provide a disposable microfluidic device designed to position a sample to be in direct contact with a high frequency vibrating element that emits an ultrasonic frequency into the sample such that the vibrational energy transduced into the sample results in fragmenting nucleic acids or disrupting cells.

14 Claims, 5 Drawing Sheets

(56) References Cited

U.S. PATENT DOCUMENTS

| | | |
|---|---|---|
| 7,323,305 B2 | 1/2008 | Leamon et al. |
| 7,335,762 B2 | 2/2008 | Rothberg et al. |
| 7,345,159 B2 | 3/2008 | Ju et al. |
| 7,425,431 B2 | 9/2008 | Church et al. |
| 7,476,504 B2 | 1/2009 | Turner |
| 7,553,949 B2 | 6/2009 | Lee et al. |
| 7,575,865 B2 | 8/2009 | Leamon et al. |
| 7,601,499 B2 | 10/2009 | Berka et al. |
| 7,635,578 B2 | 12/2009 | Ju et al. |
| 7,713,698 B2 | 5/2010 | Ju et al. |
| 7,745,116 B2 | 6/2010 | Williams |
| 7,754,429 B2 | 7/2010 | Rigatti et al. |
| 7,790,869 B2 | 9/2010 | Ju et al. |
| 7,824,887 B2 | 11/2010 | Lee et al. |
| 7,835,871 B2 | 11/2010 | Kain et al. |
| 7,842,457 B2 | 11/2010 | Berka et al. |
| 7,858,311 B2 | 12/2010 | Williams |
| 2007/0009884 A1 | 1/2007 | Stoughton et al. |
| 2007/0087362 A1 | 4/2007 | Church et al. |
| 2007/0092901 A1 | 4/2007 | Ligler et al. |
| 2007/0128610 A1 | 6/2007 | Buzby |
| 2009/0233814 A1* | 9/2009 | Bashkirov et al. .............. 506/30 |
| 2009/0318298 A1 | 12/2009 | Kim et al. |
| 2010/0096268 A1 | 4/2010 | Ling et al. |
| 2010/0137143 A1 | 6/2010 | Rothberg et al. |
| 2010/0300895 A1 | 12/2010 | Nobile et al. |
| 2010/0301398 A1 | 12/2010 | Rothberg et al. |
| 2010/0310421 A1 | 12/2010 | Oliver et al. |

OTHER PUBLICATIONS

Elsner, Henrik I. et al. "Ultrasonic degradation of DNA." DNA (1989) 8 697-701.*

Ponce, Maria R. et al. "PCR amplification of long DNA fragments." Nucleic Acids Research (1992) 623.*

Marentis, Theodore Cosmo et al. "Microfluidic sonicator for real-time disruption of eukaryotic cells and bacterial spores for DNA analysis." Ultrasound in Medicine and Biology (2005) 31 1265-1277.*

Belgrader P., et al., "A Minisonicator to Rapidly Disrupt Bacterial Spores for DNA Analysis," Analytical Chemistry, 1999, vol. 71 (19), pp. 4232-4236.

International Search Report and Written Opinion for Application No. PCT/US2012/022077, mailed on May 8, 2012, 10 pages.

* cited by examiner

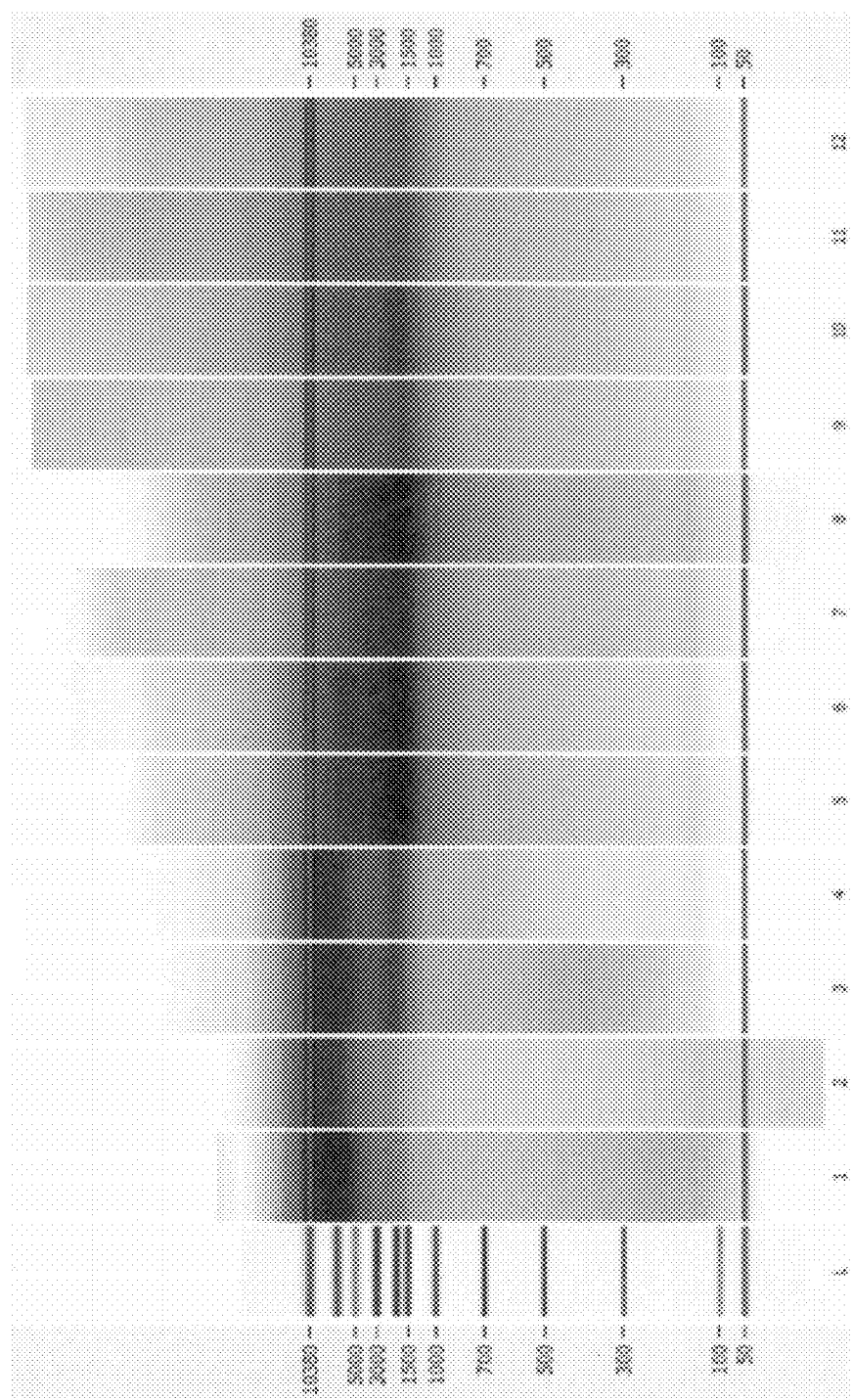

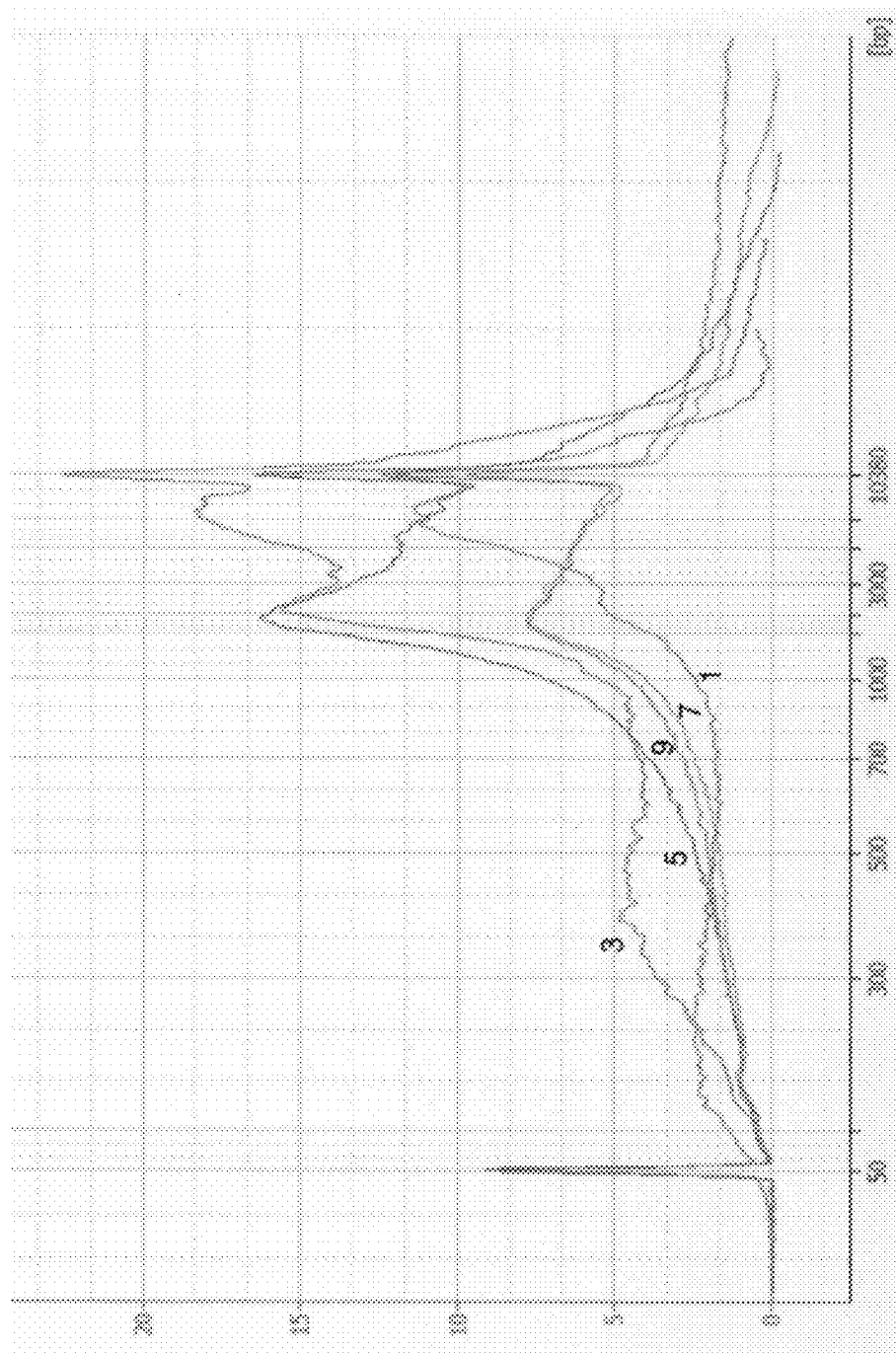

MICROFLUIDIC TRANSDUCER

The present Application claims priority to U.S. Provisional Application Ser. No. 61/434,704 filed Jan. 20, 2011, the entirety of which is incorporated by reference herein.

STATEMENT REGARDING FEDERALLY SPONSORED RESEARCH OR DEVELOPMENT

This invention was made with government support under Grant No. HDTRA1-10-C-0080 awarded by the Defense Threat Reduction Agency. The government has certain rights in the invention.

FIELD

Provided herein are apparatuses and methods for fragmenting nucleic acids or disrupting cells. For example, some embodiments provide a disposable microfluidic device designed to position a sample to be in direct contact with a high frequency vibrating element that emits an ultrasonic frequency into the sample such that the vibrational energy transduced into the sample results in fragmenting nucleic acids or disrupting cells.

BACKGROUND

Knowledge of DNA sequences has become indispensable for basic biological research and in numerous applied fields such as diagnostics, biotechnology, forensic biology, and biological systematics. While the initial advent of DNA sequencing significantly accelerated biological research and discovery, the present rapid speed of sequencing attained with modern DNA sequencing technology has been instrumental in the sequencing of the human genome and in related projects providing the complete DNA sequences of many animal, plant, and microbial genomes. Currently, next generation sequencing technologies have emerged to advance genome sequencing at unprecedented speeds, transforming biological research with a number of novel applications.

Random shotgun sequencing has been the typical method used to determine the sequence of a genome. The success and efficiency of this process is dependent on random fragmentation of DNA and cloning of these fragments to generate a shotgun library. In addition, DNA fragmentation is also the most critical sample preparation step required by all currently available next-generation sequencing platforms.

However, current fragmentation methods possess significant disadvantages that can cause them to be a weak link in the process workflow for both current and next-generation sequencing technologies. Inefficient fragmentation is one problem common to current fragmentation technologies. The resulting increased processing times and lowered yields can impart significant losses of time and resources when multiplied several-fold in today's massive, high-throughput sequencing projects.

SUMMARY

Provided herein are apparatuses and methods for fragmenting nucleic acids or disrupting cells. For example, some embodiments provide a microfluidic device (e.g., disposable) designed to position a sample to be in direct contact with a high frequency vibrating element that emits an ultrasonic frequency into the sample such that the vibrational energy transduced into the sample results in fragmenting nucleic acids or disrupting cells.

Embodiments of the present technology provide a disposable microfluidic device for fragmenting DNA or disrupting cells that may find use, for example, in preparing DNA for sequencing. In the device, a disposable ultra high frequency vibrating element is used to transduce energy into the sample. The vibrational energy causes cavitation in the sample, which imparts physical stress on DNA and cells such that DNA is fragmented and cells are disrupted.

The device's design provides several advantages. For example, positioning the sample in direct contact with the vibrating element maximizes energy transduction from the vibrating element to the sample. Also, integrating the technology in a microfluidic device minimizes sample volumes, which maximizes sample recovery and enables efficient delivery of vibrational energy throughout the entire sample. Moreover, use of a sealed, disposable device minimizes the problems of contamination and sample carry-over that can compromise projects requiring extreme sensitivity. Accordingly, it is contemplated that this technology enables the integration of an efficient, easy to use, high-throughput-capable, and highly reproducible DNA fragmentation technology into a microfluidic device that carries out the other steps involved in preparing DNA for sequencing, such as nucleic acid extraction, DNA end polishing, linker ligation, and library purification.

To this end, embodiments of the technology provide herein an apparatus (e.g., disposable) for processing a sample comprising a disposable high frequency vibrating element, wherein the sample is in direct contact with the disposable high frequency vibrating element. In some embodiments, the sample comprises nucleic acid. In some embodiments, the sample comprises cells. In some particular embodiments, the nucleic acid is DNA. Embodiments of the apparatus provided herein fragments the nucleic acid. In some embodiments, the apparatus produces nucleic acid fragments of approximately 2000 bases or base pairs. In other embodiments, the apparatus disrupts or lyses cells. Without limitation with respect to the frequencies that can be provided by the disposable high frequency vibrating element, in some embodiments, for example, the disposable high frequency vibrating element produces frequencies of 1-1000 MHz.

In some embodiments, the apparatus further comprises a sample chamber, a sample inlet connected to the sample chamber, and a sample outlet connected to the sample chamber, wherein the sample is introduced into the sample chamber via the sample inlet chamber, the sample chamber is designed to position the sample in direct contact with the disposable high frequency vibrating element, and the sample can be removed from the sample chamber via the sample outlet. Some embodiments provide that the apparatus further comprises a sealed microfluidic card, wherein the disposable apparatus is integrated into the sealed microfluidic card. Some embodiments provide an apparatus that is adapted to interface with a microfluidic system and some embodiments provide an apparatus that is adapted to interface with an external energy source, wherein the external energy source provides energy to the disposable high frequency vibrating element. Embodiments of the technology provided herein relate to an apparatus that causes cavitation in a sample. While the technology is not limited in the sample sizes that can be accommodated, the microfluidic platform provides for the use of small (e.g., microliter, nanoliter) sample sizes, For example, some embodiments provide an apparatus with a sample chamber having a volume of approximately 200 microliters.

Also provided herein are embodiments of methods for fragmenting nucleic acids comprising positioning a sample comprising a nucleic acid in direct contact with the disposable high frequency vibrating element of the apparatus described above and transducing energy from the disposable high frequency vibrating element into the sample. While not limited in the size of fragments that can be produced with the present technology, in some embodiments, for example, the energy transduction is tuned to produce a collection of nucleic acid fragments having a distribution of lengths centered on approximately 2000 bases or base pairs. In addition, in some embodiments the collection of nucleic acid fragments comprises an unbiased set of fragments.

Also provided herein is a system for fragmenting a nucleic acid sample comprising a means to produce an ultrasonic frequency capable of fragmenting DNA, a means to hold the sample in direct contact with the means of producing the ultrasonic frequency, and a means to transduce the ultrasonic frequency into the sample.

The devices and methods provided herein may be used with (e.g., integrated into) systems for next-generation sequencing including, but not limited to, technologies comprising sequencing-by-synthesis, polony sequencing (e.g., U.S. Pat. No. 7,425,431; U.S. Pat App. No. 20090318298; 20070087362, incorporated herein in their entireties for all purposes), fluorescently-labeled terminator sequencing, sequencing by ligation using fluorescently labeled di-base probes, sequencing by detecting pH or voltage changes from the release of hydrogen ions, single molecule sequencing, nanopore sequencing, sequencing by hybridization, carbon nanotube field effect transistor sequencing, and strobe sequencing, and the like, as implemented in technologies provided, e.g., by Roche (454 Life Sciences and/or Curagen) (e.g., U.S. Pat. Nos. 7,842,457; 7,601,499; 7,575,865; 7,335,762; 7,323,305; 7,264,929; 7,244,567; 7,244,559; 7,211,390; and 6,274,320, incorporated herein by reference in their entireties for all purposes), Illumina Inc. (Solexa Inc. and/or Lynx Therapeutics) (e.g., U.S. Pat. Nos. 6,013,445; 7,835,871; 7,754,429; 7,115,400; 5,750,341; 5,969,119; 6,306,597; and 6,833,246, incorporated herein by reference in their entireties for all purposes), Life Technologies (Applied Biosystems Inc. and/or Agencourt Personal Genomics and/or Applera) SOLiD sequencing (e.g., U.S. Pat. Nos. 7,824,887; 7,553,949, incorporated herein by reference in their entireties for all purposes), Pacific Biosciences (e.g., U.S. Pat. Nos. 7,858,311; 7,745,116; 7,476,504, incorporated herein in their entireties for all purposes), Life Technologies Ion Torrent sequencing (e.g., U.S. Pat. App. No. 20100300895; 20100301398; 20100137143, incorporated herein in their entireties for all purposes), Helicos Biosciences Corp. (e.g., U.S. Pat. No. 7,169,560, incorporated herein by reference in its entirety for all purposes), NABsys Inc. (e.g., U.S. Pat. App. Nos. 20100096268; 20100310421, incorporated herein in their entireties for all purposes), Intelligent Bio-Systems (e.g., U.S. Pat. Nos. 6,664,079; 7,635,578; 7,713,698; 7,790,869; 7,345,159, incorporated herein in their entireties for all purposes), and the like.

Additional embodiments will be apparent to persons skilled in the relevant art based on the teachings contained herein.

DESCRIPTION OF THE DRAWINGS

These and other features, aspects, and advantages of the present technology will become better understood with regard to the following drawings:

FIG. 4 shows a scan of an electrophoresis gel used to separate fragmented nucleic acid samples. Twelve lanes are labeled at the bottom and approximate sizes of nucleic acids are indicated along the left and right sides.

FIG. 5 shows a densitometric plot of an electrophoresis gel used to separate fragmented nucleic acid samples. Relative fluorescence intensity is plotted versus approximate size in base pairs for a subset of the samples shown in FIG. 4.

DETAILED DESCRIPTION

Figure 1:
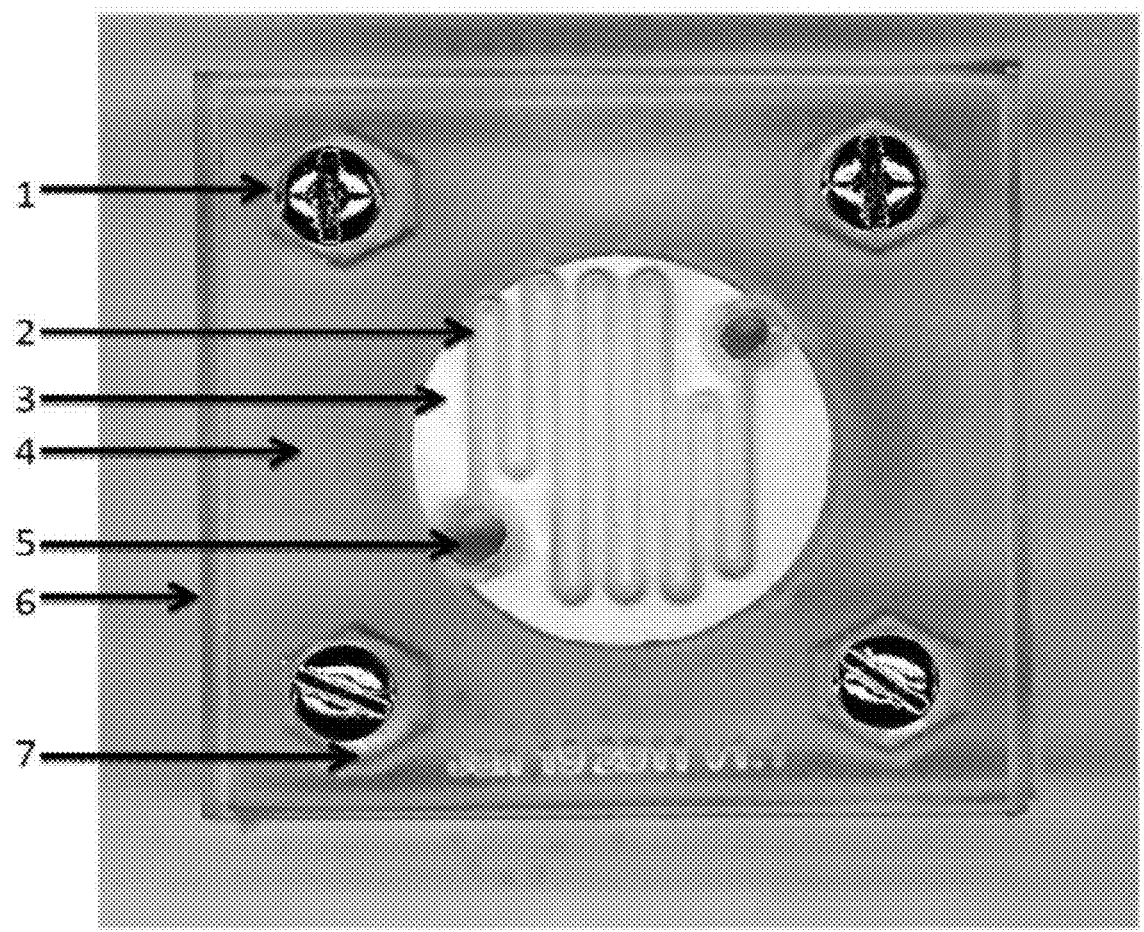
FIG. 1 shows an embodiment of the technology as a prototype flow-through microfluidic sample preparation card comprising an integrated high frequency vibrating element 3, a microfluidic serpentine channel 2, and an inlet or outlet port 5.

Provided herein are apparatuses and methods for fragmenting nucleic acids or disrupting cells. For example, some embodiments provide a disposable microfluidic device designed to position a sample to be in direct contact with a high frequency vibrating element that emits an ultrasonic frequency into the sample such that the vibrational energy transduced into the sample results in fragmenting nucleic acids or disrupting cells.

Definitions

To facilitate an understanding of the present technology, a number of terms and phrases are defined below. Additional definitions are set forth throughout the detailed description.

As used herein, "a" or "an" or "the" can mean one or more than one. For example, "a" cell can mean one cell or a plurality of cells.

As used herein, a "transducer" is a device that converts one type of energy to another. The conversion can be to or from electrical, electro-mechanical, electromagnetic, photonic, photovoltaic, or any other form of energy. While the term transducer commonly implies use as a sensor or detector, any device which converts energy can be considered a transducer. For example, embodiments of the technology provided herein incorporate a transducer that converts electrical energy to mechanical energy in the form of sound waves of a specific frequency.

As used herein, the term "sample" is used in its broadest sense. In one sense it can refer to animal cells or tissues. In another sense, it is meant to include a specimen or culture obtained from any source, such as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present technology.

Embodiments of the Technology

Although the disclosure herein refers to certain illustrated embodiments, it is to be understood that these embodiments are presented by way of example and not by way of limitation.

1. Ultrasonic Vibrating Element

Embodiments of the technology provided herein comprise a vibrating element to generate ultrasonic frequencies. The ultrasonic vibrating element may be any device, apparatus, manufacture, composition, or other item that can generate the appropriate frequencies for fragmenting DNA or disrupting cells in a microfluidic device. For example, in some embodiments the vibrating element is a transducer that converts electrical energy into mechanical energy, e.g., in the form of sound waves. Types of transducers contemplated for use in the present methods, apparatuses, and systems include, but are not limited to, piezoelectric and magnetostrictive transducers. In an exemplary embodiment of the technology, a piezoelectric transducer is used to contact a sample directly and provides a frequency of 2.4 MHz. The dimensions of a suitable vibrating element are on the order of approximately less than a meter, e.g., on the order of less than ten centimeters.

2. Microfluidic Devices

Contemplated herein is the use of an ultrasonic vibrating element in a microfluidic device used to process biological samples. For example, fragmentation of nucleic acids is a key step for the preparation of DNA libraries for sequencing. It is contemplated that the present technology enables the integration of this key process into a microfluidic device that carries out the other steps involved in DNA sequencing library preparation, e.g., nucleic acid extraction, DNA end polishing, linker ligation, and library purification. The ability to disrupt cells or fragment nucleic acid (e.g., DNA) rapidly and efficiently in a closed microfluidic device provides advantages over previous methods, e.g., more efficient energy transfer into the sample that can result in, e.g., decreased preparation time. In addition, the microfluidic format results in increased sample recovery and using a disposable vibrating element in the microfluidic device can allow decreased incidence of contamination and sample carry-over.

Also contemplated herein is the use of an ultrasonic vibrating element in a microfluidic device adapted for other molecular biological and biochemical applications, e.g., analysis of enzyme kinetics, thermodynamics, and inhibition; DNA analysis (e.g., polymerase chain reaction (PCR) and digital PCR); proteomics; DNA microarrays; protein microarrays; and immunological assays, etc. The microfluidic ultrasonic frequency generator may also find use in microfluidics adapted for electrophoresis, two-dimensional electrophoresis, transcriptome analysis, liquid chromatography, cell separation (e.g., blood cell separation), cell manipulation, and cell capture, including the capture and isolation of microorganisms. In addition, microfluidics-based devices, capable of continuous sampling and real-time testing of environmental samples for biochemical toxins and other dangerous pathogens, can serve as an always-on sentry for the detection of biological contamination or bioterror agents. The size of the microfluidic device is appropriate for laboratory-scale research, e.g., appropriate for placing on a bench top. Accordingly, the microfluidic device has dimensions on a scale of approximately less than a meter, e.g., approximately less than ten centimeters.

In an exemplary embodiment shown in FIG. 1, the ultrasonic vibrating element 3 (e.g., a gold crystal) is embedded in a sealed, flow-through microfluidic sample preparation card 4. As shown, the microfluidic sample preparation card 4 includes a membrane gasket 6 disposed between polyacrylic housing elements that are held together via tightening screws 1 and hex nuts 7. The hex nuts 7 are disposed in countersink etches in one of the polyacrylic housing elements. A sample chamber 2 (shown as a microfluidic serpentine channel) in the microfluidic sample preparation card 4 holds a sample for processing, i.e., by exposure to ultrasonic frequencies. The sample chamber 2 is designed to position the sample to be in direct contact with the ultrasonic vibrating element 3. A sample inlet port 5 and a sample outlet port provide fluid interconnections to the sample chamber 2 for the introduction of sample into the sample chamber 2 (e.g., by upstream microfluidic devices) and recovery of the processed sample from the sample chamber 2 (e.g., for further processing by downstream microfluidic devices). Thus, the sample flows in through one port, into the sample chamber, and then out the other port. Accordingly, the microfluidic sample preparation card 4 would be adapted to connect to other microfluidic devices by fluid interconnections and it is contemplated that other external microfluidics would drive the movement of samples into and out of the sample processing card 4. An external power supply interfaces with the sample card to provide the power required to drive the ultrasonic frequency generator.

EXAMPLES

Example 1

During the development of embodiments of the technology provided herein, prototypes were constructed to demonstrate the effectiveness of the technology in fragmenting nucleic acids. The prototype assemblies used a 2.4 MHz gold-coated nebulizer crystal (Sonaer, Inc. Cat. No. 24AU), electronics to energize the vibrating element (Sonaer, Inc. Cat. No. 241CST), and custom re-useable machined parts designed to simulate the environment within the contemplated microfluidic sample processing card. The power supply was connected to a switch that allowed an external device to control the on/off duty cycle.

Figure 2:
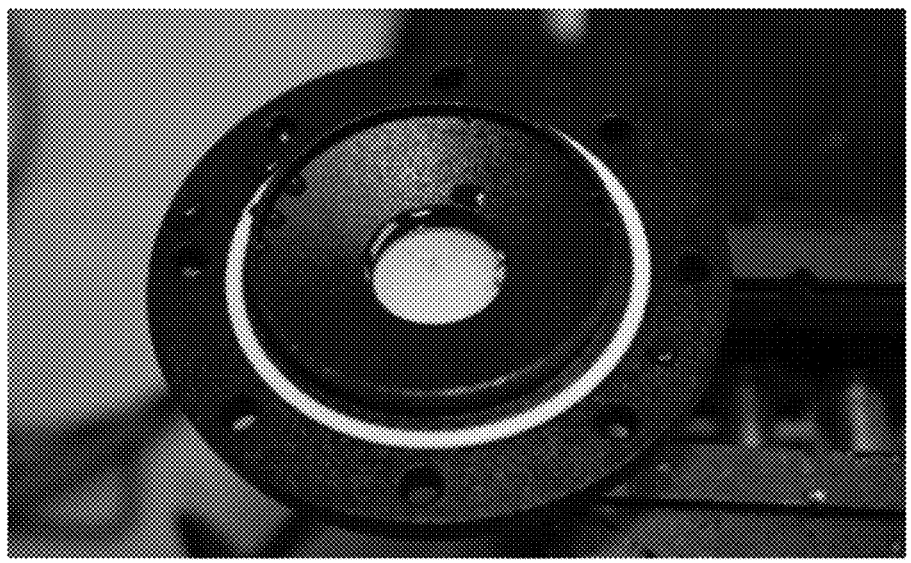
FIG. 2 shows a top view (FIG. 2A) and a side view (FIG. 2B) of an embodiment of the technology as a first prototype device for fragmenting nucleic acids.
Figure 2:
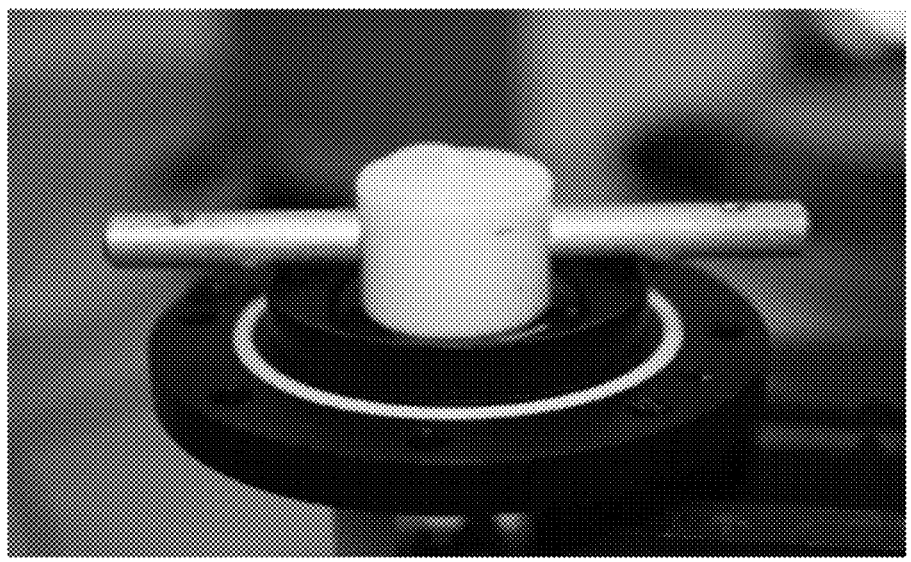
Figure 3:
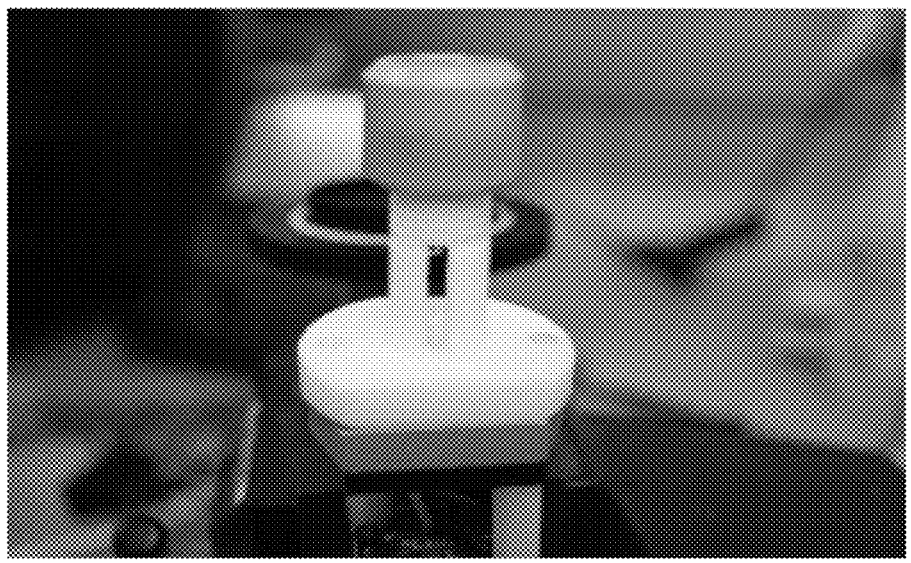
FIG. 3 shows an embodiment of the technology as a second prototype device for fragmenting nucleic acids.

A first prototype (see FIG. 2) was designed to hold a static volume of about 200 microliters. The sample was loaded directly on the vibrating element and then sealed with a Teflon cap. A second prototype (see FIG. 3) was designed to hold larger volumes and allows the operator to view the sample during processing via a viewing area.

Example 2

During the development of embodiments of the technology provided herein, it was demonstrated that the technology can produce fragmented nucleic acids of about 2000 base pairs. Using the second prototype, DNA samples were fragmented using a frequency of 2.4 MHz. A 24 V AC, 0.8 A power supply was used to provide a 5-s on/off duty cycle. Samples were subjected to fragmentation for times ranging from 30 to 120 s. As assessed by electrophoresis (FIG. 4), the technology produced DNA fragments of approximately 2 kbp from starting material comprising molecules of a longer length (approximately 10 kbp). Unfragmented input DNA sample comprised lengths of approximately 5 to 10 kbp (lanes 1 & 2). Processing in prototype 2 produced fragments of smaller sizes (lanes 3-12). Experiments were performed in which samples were exposed to the ultrasonic frequency for 30 s (lanes 3 & 4), 60 s (lanes 5 & 6), 90 s (lanes 7 & 8), and 120 s (lanes 9-12). L marks the DNA fragment size ladder standard.

Size distributions of the electrophoresed fragmented samples were determined by densitometry using relative fluorescence intensity as a measure of DNA quantity (FIG. 5). Quantification of the DNA fragments shows the production of fragments of approximately 2 kbp. Samples from lanes 1, 3, 5, 7, and 9 above were quantified (FIG. 5).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. An apparatus for processing a sample comprising nucleic acid comprising a disposable high frequency vibrating transducer tuned to produce a collection of nucleic acid fragments having a distribution of lengths centered on approximately 2000 bases or base pairs, wherein the sample is in direct contact with the disposable high frequency vibrating transducer.

2. The apparatus of claim 1, wherein the sample comprises cells.

3. The apparatus of claim 1, wherein the nucleic acid is DNA.

4. The apparatus of claim 2, wherein the apparatus disrupts or lyses cells.

5. The apparatus of claim 1, wherein the disposable high frequency vibrating transducer produces frequencies of 1-1000 MHz.

6. The apparatus of claim 1, further comprising a sample chamber, a sample inlet connected to the sample chamber, and a sample outlet connected to the sample chamber, wherein the sample is introduced into the sample chamber via the sample inlet, the sample chamber is designed to position the sample in direct contact with the disposable high frequency vibrating transducer, and the sample can be removed from the sample chamber via the sample outlet.

7. The apparatus of claim 1, further comprising a sealed microfluidic card wherein the disposable high frequency vibrating transducer is integrated into the sealed microfluidic card.

8. The apparatus of claim 1, adapted to interface with a microfluidic system.

9. The apparatus of claim 1, adapted to interface with an external energy source, wherein the external energy source provides energy to the disposable high frequency vibrating transducer.

10. The apparatus of claim 1, wherein the apparatus causes cavitation in the sample.

11. The apparatus of claim 5, wherein the sample chamber has a volume of approximately 200 microliters.

12. A method for fragmenting nucleic acids comprising:
   a) positioning a sample comprising a nucleic acid in direct contact with the disposable high frequency vibrating transducer of the apparatus of claim 1; and
   b) transducing energy from the disposable high frequency vibrating transducer into the sample.

13. The method of claim 12, wherein the collection of nucleic acid fragments comprises an unbiased set of fragments.

14. A system for fragmenting a nucleic acid sample comprising a first component comprising an electrical energy source that produces an ultrasonic frequency capable of fragmenting DNA, a second component comprising a microfluidic channel comprising an inlet port and an outlet port that holds the sample in direct contact with the first component, and a third component comprising, and a transducer in direct contact with the first component and the second component said electrical energy source and said microfluidic channel tuned to produce a collection of nucleic acid fragments having a distribution of lengths centered on approximately 2000 bases or base pairs that transduces the ultrasonic frequency into the sample.

* * * * *